United States Patent [19]
Gherson et al.

[11] Patent Number: 5,817,955
[45] Date of Patent: Oct. 6, 1998

[54] APPARATUS FOR SIMULTANEOUS ASPIRATION AND DISPENSATION OF FLUIDS

[75] Inventors: Paul Gherson, Yorktown Heights; Carl Gebauer, Granite Springs, both of N.Y.

[73] Assignee: Bayer Corporation, Tarrytown, N.Y.

[21] Appl. No.: 828,969

[22] Filed: Mar. 27, 1997

Related U.S. Application Data

[63] Continuation of Ser. No. 620,702, Mar. 21, 1996, abandoned.

[51] Int. Cl.[6] .................................................. F04B 39/10
[52] U.S. Cl. .................................... 73/864.35; 417/535
[58] Field of Search ........................ 73/863.32, 864.13, 73/864.16–864.18, 864.35; 417/521, 531, 534, 555.1, 556, 491, 402, 535, 536

[56] References Cited

U.S. PATENT DOCUMENTS

| | | |
|---|---|---|
| 281,695 | 7/1883 | Holcombe . |
| 3,043,497 | 7/1962 | Knobloch et al. . |
| 3,238,889 | 3/1966 | Huber et al. . |

FOREIGN PATENT DOCUMENTS

| | | |
|---|---|---|
| 953 921 | 4/1964 | United Kingdom . |

*Primary Examiner*—Robert Raevis
*Attorney, Agent, or Firm*—Andrew L. Klawitter; Rodman & Rodman

[57] ABSTRACT

The apparatus for simultaneous aspiration and dispensation of fluids is in the form of a syringe with two chambers located end to end along the length of the syringe. Each syringe chamber includes a port. A piston inside the syringe includes a median section that is movable in both of the syringe chambers, a first end section movable only in one of the syringe chambers, and a second end section movable only in the other syringe chamber. Both end sections of the piston are of either less diameter than the median section of the piston or of greater diameter than the median section of the piston. When the piston is moved in a first direction, an aspiration or suction force is developed at one of the chamber ports and a dispensation pressure force is developed at the other chamber port. Reverse movement of the piston causes the opposite effect at the respective chamber ports. A compression seal is provided at the median section of the piston and at opposite non-adjacent end portions of the syringe chambers. The syringe housing can be formed in two separable sections to permit access to the compression seal at the median portion of the piston. Tandem compression seals can also be provided at the median section of the piston.

13 Claims, 2 Drawing Sheets

APPARATUS FOR SIMULTANEOUS ASPIRATION AND DISPENSATION OF FLUIDS

This is a continuation of application Ser. No. 08/620,702, filed Mar. 21, 1996, now abandoned.

BACKGROUND OF THE INVENTION

This invention relates to multi-function devices that operate on fluid, and more particularly to a syringe with a single piston and two chambers for simultaneous aspiration of fluid into one chamber, dispensation of fluid from the other chamber and vice versa.

Analysis systems for sample liquids, such as shown in U.S. Pat. No. 5,268,147, perform multiple tests on numerous different liquid samples, automatically and at relatively high speed. Sample test operation procedures typically include aspiration of sample fluid and/or reagent from one or more sources, and subsequent dispensation of the aspirated fluid for test or analysis. In some instances, because of timing considerations or other operational requirements, it is desirable to simultaneously perform a separate aspiration operation on one fluid sample and a separate dispensation operation on another fluid sample.

Simultaneous aspiration of one fluid sample and dispensation of another fluid sample is usually accomplished with separate metering and/or displacement pumps for each respective fluid sample that is to be simultaneously treated, with the pumps arranged to operate in synchronized fashion. The electrical coordination and mechanical cooperation needed to obtain synchronized operation of two or more pumps may require complex circuitry and cumbersome networks of pumping systems. Should there be any disparities in the expected synchronization of multiple pump operation, such as, for example, due to different levels of frictional drag within the pumps, the test results can be flawed.

It is known, as shown in U.S. Pat. Nos. 3,640,434 and 4,679,446, to provide a pipette that simultaneously dispenses fluid from two or more separate chambers in a syringe, using a single displacement actuator. However, none of the disclosed pipettes have the capability of simultaneously dispensing one fluid sample from one chamber and aspirating another fluid sample from another chamber.

It is also known, as shown in U.S. Pat. Nos. 4,941,808 and 5,383,372 to provide a pipette with two separate pistons in a single chamber to sequentially aspirate and dispense fluid. Because of the single chamber arrangement, the incoming aspirated fluid and the outgoing dispensed fluid can intermix and cause cross-contamination. Furthermore, the disclosed single chamber structure cannot simultaneously aspirate and dispense separate isolated samples of fluid with one-directional movement of a single piston.

It is thus desirable to provide a syringe or pipette which can simultaneously aspirate and dispense separate isolated samples of fluid upon movement of a single piston member in one direction.

OBJECTS AND SUMMARY OF THE INVENTION

Among the several objects of the invention may be noted the provision of a novel apparatus for simultaneous aspiration and dispensation of fluid, a novel apparatus for simultaneous aspiration and dispensation of separate isolated samples of fluid, a novel apparatus for simultaneous aspiration and dispensation of fluid wherein a single piston is operable in two separate noncommunicable chambers, a novel syringe having a single piston adapted to cause fluid dispensation from one chamber of a syringe while causing fluid aspiration into another chamber of the syringe, a novel piston-actuated apparatus for simultaneous aspiration and dispensation of fluid wherein a piston moving in one direction causes simultaneous aspiration and dispensation of separate isolated fluid samples, a novel syringe having a single piston and two separate chambers, wherein movement of the piston in one direction aspirates one fluid sample into one chamber and dispenses another fluid sample from another chamber, and a novel method of simultaneously aspirating and dispensing fluid.

Other objects and features of the invention will be in part apparent and in part pointed out hereinafter.

In accordance with the invention, the apparatus for simultaneous aspiration and dispensation of fluids is in the form of a syringe. The syringe includes a syringe body that defines first and second elongated chambers that are arranged end to end and are non-communicable in the syringe body. Each of the syringe chambers has a port for both inlet and outlet of fluid. Thus, each chamber port is a dual purpose port and is used for both aspiration and dispensation of fluid. If desired, more than one dual purpose port can be provided for each chamber.

An elongated piston is slidably disposed in the syringe and extends through the first and second elongated chambers. The piston has a first section movable in the first chamber and a second section movable in the second chamber. The syringe also includes a median section joining the first and second piston sections. The median section of the piston is movable in the first and second chambers. The first and second sections of the piston are of respective diameters that differ from the diameter of the median section of the piston. However, the diameter of the median section of the piston is either greater than or less than the diameters of each of the first and second piston sections.

In one embodiment of the invention, the first and second piston sections have diameters of less magnitude than the diameter of the median section of the piston. The first and second piston sections can be of equal diameter or they can be of different diameter, provided they are both of less magnitude than the diameter of the median section of the piston.

In another embodiment of the invention, the first and second piston sections have diameters of greater magnitude than the diameter of the median section of the piston. The first and second piston sections can be of equal or different diameter, provided that such diameters are of greater magnitude than the diameter of the median section of the piston.

In several embodiments of the invention, an annular compression seal is provided at a fixed position in the syringe body to separate the first chamber from the second chamber. The compression seal embraces the median portion of the piston to form a leak-tight seal. A compression seal is also provided at each of the non-adjacent opposite ends of the syringe body at a fixed position to embrace the first and second sections of the piston in a leak-tight seal.

In several embodiments of the invention, the syringe body is constituted as two separable sections, with one of the chambers being located in one of the body sections and the other of the chambers being located in the other body section. Separation of the syringe body sections permits access to the compression seal that separates the chambers. Separation of the body sections also permits access to the piston member and to the chambers within the syringe body.

In another embodiment of the invention, a pair of annular compression seals are provided intermediate the opposite ends of the syringe body to embrace the median section of the piston in leak-tight fashion. The pair of compression seals are in a tandem relationship and can either be in contact with each other or spaced slightly from each other.

Under this arrangement, movement of the piston in one direction causes aspiration suction at one chamber port of the syringe and simultaneous dispensation pressure at the other chamber port of the syringe. When the piston moves in an opposite direction, the reverse action occurs, i.e., dispensation pressure is provided at the one chamber port and aspiration suction is provided at the other chamber port.

The invention also includes a method for simultaneous aspiration and dispensation of fluid. The method includes forming a syringe body with two chambers that do not communicate within the syringe body, providing a port for each chamber to permit each chamber to aspirate and dispense fluid, and slidably disposing an elongated piston in the syringe body to extend through both chambers of the syringe body. The method further includes forming the piston with a median section that is movable in both the first and second chambers of the syringe body and further forming the piston with first and second end sections that are respectively movable in the first and second chambers of the syringe body. The method also requires that the diameter of the median section of the piston be formed with a different magnitude than the diameters of the first and second piston end sections, whereby the diameter of the median section is either greater or less than the diameter of each of the first and second piston end sections.

The invention accordingly comprises the constructions and method hereinafter described, the scope of the invention being indicated in the claims.

DESCRIPTION OF THE DRAWING

In the accompanying drawing.

Corresponding reference characters indicate corresponding parts throughout the several views of the drawings.

DETAILED DESCRIPTION OF THE INVENTION

Figure 1:
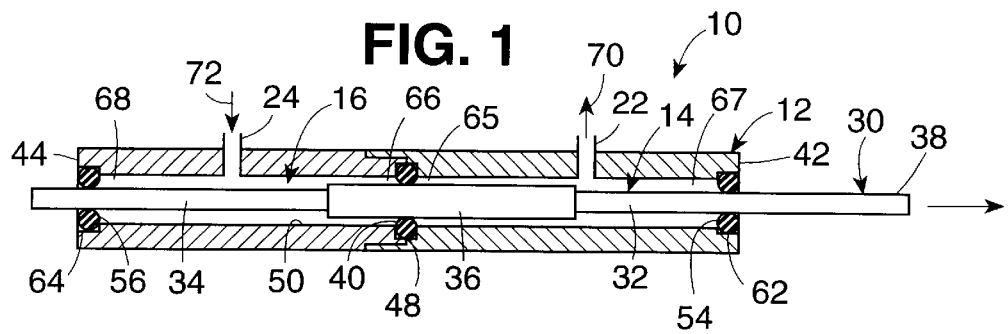
FIG. 1 is a simplified schematic view, partly shown in section, of an aspiration and dispensation apparatus incorporating the present invention.

An apparatus for the simultaneous aspiration and dispensation of fluids incorporating one embodiment of the invention is generally indicated by the reference number 10 in FIG. 1.

The apparatus 10 includes a syringe body or housing 12 having two separate chambers 14 and 16 located end to end. The syringe body 12 can be formed of any suitable glass, metal, or plastic material, for example. The chamber 14 has an inlet and outlet port 22, and the chamber 16 has an inlet and outlet port 24.

An elongated piston 30, which can be formed of stainless steel, plastic, or ceramic material, for example, is slidably disposed in the syringe body 12 for reciprocal movement in the chambers 14 and 16. The piston 30 has a first section 32, movable only in the chamber 14, and a second section 34, movable only in the chamber 16. A median section 36 of the piston joins the first and second piston sections 32 and 34, and is movable in both of the chambers 14 and 16.

Figure 6:
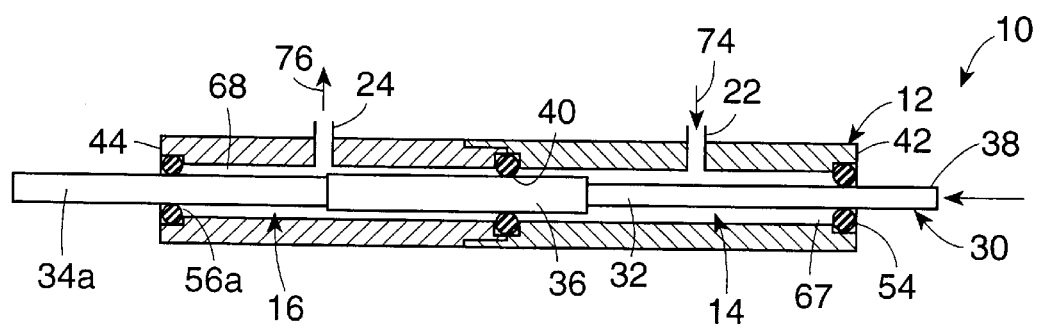

The piston 30 is preferably circular in cross-section and the diameter of the median section 36 is of greater magnitude than the diameter of the first piston section 32 and the second piston section 34. If desired, the diameters of the piston sections 32 and 34 can be substantially equivalent, or they can differ from one another provided that the diameter of each piston section 32 and 34 is less than the diameter of the median section 36 as shown in FIG. 6.

A generally annular compression seal or O-ring 40, which can be formed of high density polyethylene or Teflon®, for example, is provided inside the syringe body 12 intermediate opposite ends 42 and 44 of the syringe body. The compression seal 40 can be located at the exact mid-point between the opposite ends 42 and 44 of the syringe body 12, or at some other selected location.

The compression seal 40 is seated in an annular recess 48 at an inside surface 50 of the syringe body 12. Under this arrangement, the compression seal 40 is at a fixed position inside the syringe body 12. Additional compression seals or O-rings 54 and 56 are provided at the opposite ends 42 and 44 of the syringe body 12 in respective recesses 62 and 64 at the inside surface 50 of the syringe body 12. Under this arrangement, the compression seals 54 and 56 are held in a fixed position in the syringe body 12.

The compression seals 40, 54 and 56 are sized to tightly embrace the respective piston sections 36, 32 and 34 to provide leak-tight seals at the piston 30 and at the inside surface 50 of the syringe body 12. Thus the syringe chamber 14, which is defined between the compression seals 54 and 40, and the syringe chamber 16, which is defined between the compression seals 40 and 56, are separate and non-communicable within the syringe body 12.

The syringe chambers 14 and 16 have adjacent ends 65 and 66 at the compression seal 40 and opposite non-adjacent ends 67 and 68 at the compression seals 54 and 56.

An end 38 of the piston 30 at the first piston section 32, is connected in any suitable known manner to a known reciprocating mechanism (not shown) that provides reciprocal movement to the piston 30. The stroke of the piston 30 in either direction of movement is less than the length of the median section 36.

In using the apparatus 10, it is contemplated that such apparatus will replace conventional syringes that are usually operated in a coupled mode to obtain simultaneous aspiration and dispensation functions. However, it is also contemplated that the apparatus 10 can be used as a manually operable device for performing simultaneous aspiration and dispense functions, and vice versa, for applications where such functions are desired.

Referring to FIG. 1, the apparatus 10 is operated with reciprocating movement of the piston 30 at any selected frequency or, if desired, at any specific time lapse that can be controlled automatically in a known manner. When the piston 30 is moved to the right, as shown in FIG. 1, the median piston section 36 moves out of the chamber 16 into the chamber 14. The chamber 14 loses volume as more of the median piston section 36 moves into the chamber 14, causing an outward dispensation pressure at the port 22, as shown by the arrow 70. The simultaneous departure of the median piston section 36 from the syringe chamber 16 expands the volume of the chamber 16, causing an aspiration or suction force at the port 24, as indicated by the arrow 72.

Figure 2:
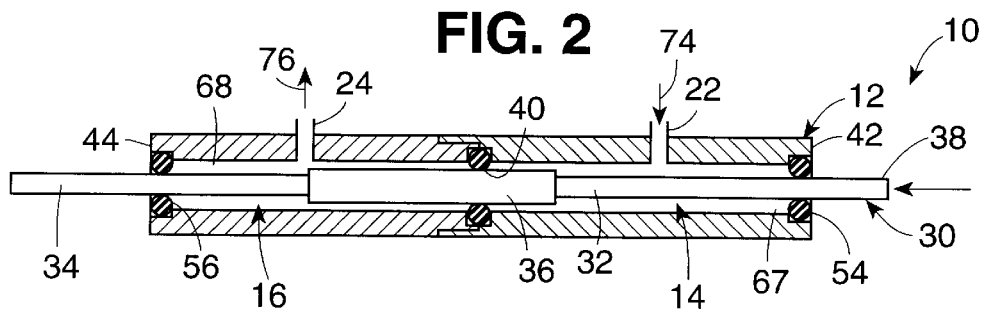
FIG. 2 is a view similar to FIG. 1 showing alternate aspiration and dispensation functions of the apparatus when the piston moves opposite to the direction shown in FIG. 1.

Reverse movement of the piston 30, as shown in FIG. 2, causes an aspiration or suction force indicated by the arrow 74 at the port 22 and a dispensation pressure force indicated by the arrow 76 at the port 24. The ports 22 and 24 can be connected to fluid lines (not shown).

In accordance with movement of the piston 30 as shown in FIG. 1, fluid will be dispensed through the port 22 per arrow 70 and simultaneously aspirated into the port 24 per arrow 72. Reverse movement of the piston 30, as shown in FIG. 2, will cause aspiration of fluid per the arrow 74 into the port 22 of the chamber 14 and dispensation of fluid out of the port 24 of the chamber 16 per the arrow 76.

Figure 3:
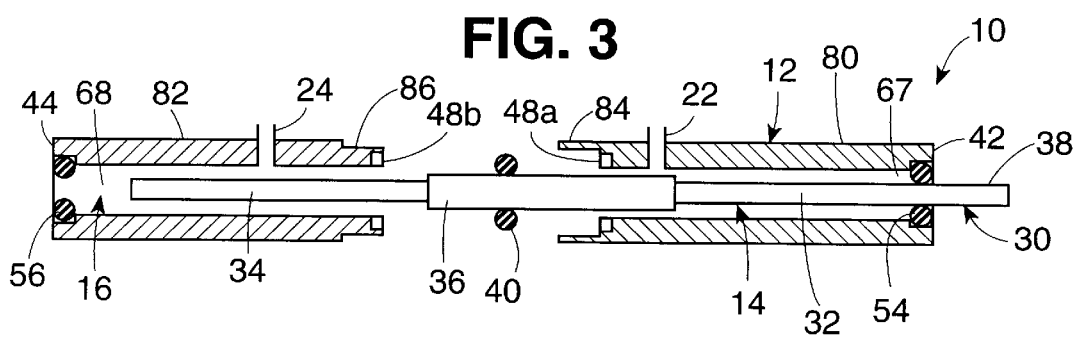
FIG. 3 is a view similar to FIG. 1 showing the apparatus in a separated condition.

As most clearly shown in FIG. 3, the syringe body 12 can be formed in two detachable body sections 80 and 82. The body section 80 has a female end portion 84 engageable with a male end portion 86 of the body section 82. The female and male engagement portions 84 and 86 can be detachably secured together in any suitable known manner.

Each of the female and male engagement portions 84 and 86 include a part of the annular recess 48 for the compression seal 40. Thus, an annular recess portion 48a is located in the female portion 84 and an annular recess portion 48b is located in the male portion 86. Separation of the body sections 80 and 82 permits access to the compression seal 40 for servicing or replacement, and also permits convenient access to the piston 30 for inspection, repair or replacement. In addition, the chambers 14 and 16 of the syringe body 12 are accessible for inspection and cleaning, for example.

It is thus apparent that axial motion of the piston 30 displaces a volume within each chamber 14 and 16 equal to the difference in volume between portions of the piston that enter and leave the respective chambers. The volumetric differences in each of the two chambers 14 and 16 due to piston movement can be made equal or made to a specific ratio by the choice of piston diameter at the piston sections 32, 34 and 36. The exact volume displaced in each chamber is substantially equivalent to the difference in cross-sectional area of the two diameters of the piston, multiplied by the distance traveled by the piston. In some instances, it may be desirable that one chamber be longer than the other chamber.

Figure 4:
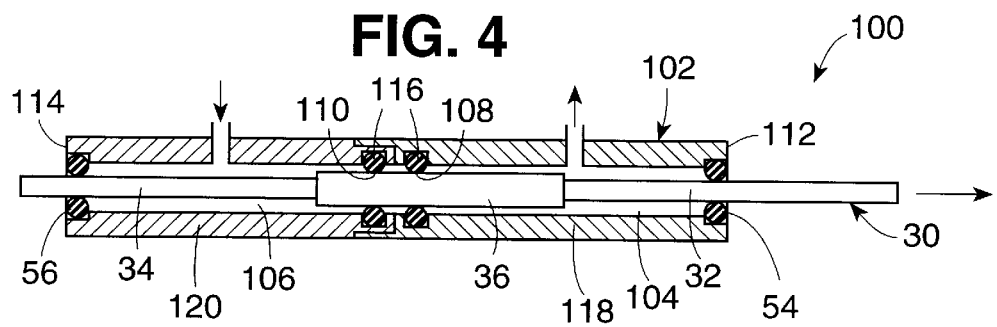
FIGS. 4 and 5 are simplified schematic views, partly shown in section, of other embodiments of the invention; and, FIGS. 6 and 7 are simplified schematic views, partly shown in section, of still other embodiments of the invention.

Another embodiment of the apparatus for simultaneous aspiration and dispensation of fluids is generally indicated by the reference number 100 in FIG. 4. The apparatus 100 includes a syringe body 102 with chambers 104 and 106 similar to the chambers 14 and 16 of the apparatus 10. However, the apparatus 100 differs from the apparatus 10 by provision of two compression seals 108 and 110 intermediate opposite ends 112 and 114 of the syringe body 102. Each compression seal 108 and 110 is disposed in an annular recess 116 similar to the annular recess 48 previously described, to fix the position of such compression seals 108 and 110 in the syringe body 102. The apparatus 100 is otherwise identical to the apparatus 10.

Thus, the apparatus 100 includes body sections 118 and 120 that are detachable from each other in the manner previously described for the apparatus 10. Under this arrangement, separation of the body sections 118 and 120 provides access to the compression seals 108 and 110, the piston 30 and the piston chambers 104 and 106. The apparatus 100 operates in a manner similar to that previously described for the apparatus. 10.

Figure 5:
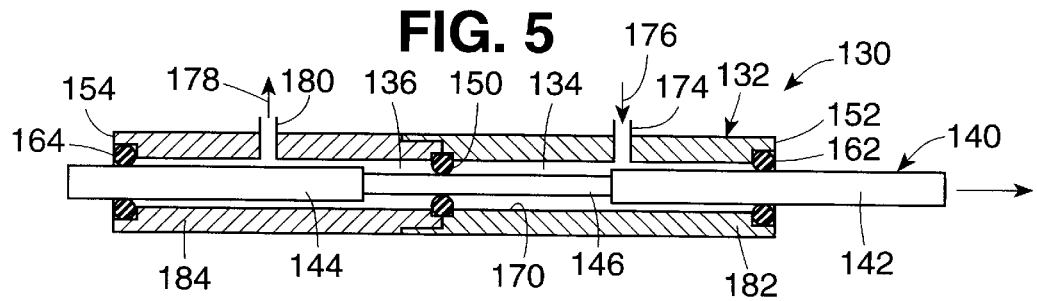

Another embodiment of the apparatus for simultaneous aspiration and dispensation of fluid is generally indicated by the reference number 130 in FIG. 5. The apparatus 130 includes a syringe body 132 having chambers 134 and 136.

A piston 140 is slidably disposed in the syringe body 132 for movement in the chambers 134 and 136. The piston 140 includes a first piston section 142, a second piston section 144, and a median piston section 146 that joins the piston sections 142 and 144.

Figure 7:
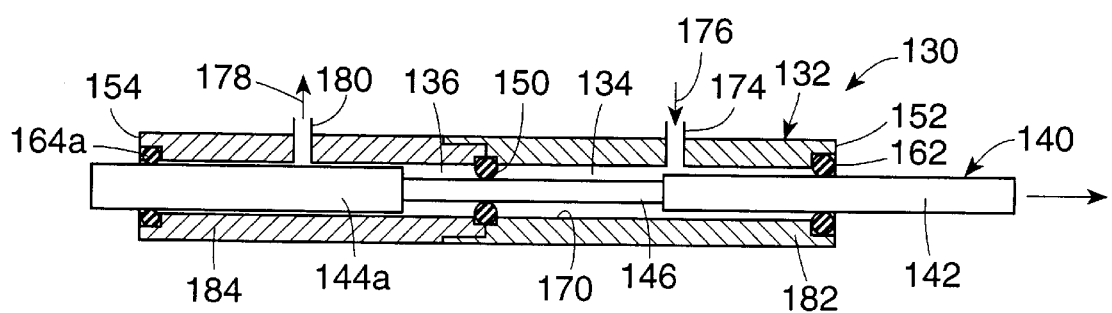

As will be seen from FIG. 5, the piston sections 142 and 144 are of greater diameter than the diameter of the median piston section 146. The piston sections 142 and 144 can be of equal diameter or of different diameter, provided that both piston sections 142 and 144 are of greater diameter than the median piston section 146 as shown in FIG. 7.

A compression seal or O-ring 150 is provided in the syringe body 132 intermediate opposite ends 152 and 154 of the syringe body 132. Compression seals 162 and 164 are also provided at the opposite ends 152 and 154 of the syringe body 132. The compression seals 150, 162 and 164 are located in a fixed position on the inside surface 170 of the syringe body 152 in annular recesses in a manner similar to that previously described for the compression seals 40, 62 and 64 of the apparatus 10. The compression seals 150, 162 and 164 form a leak-tight seal between the inner surface 170 of the syringe body and the respective piston sections 146, 142 and 144.

Operation of the apparatus 130 will be described for movement of piston 140 in the direction indicated. Movement of the piston 140 as shown causes an aspiration suction force indicated by the arrow 176 at a port 174 of the chamber 134. Movement of the piston 140 in the direction shown also causes a dispensation pressure force indicated by the arrow 178 at a port 180 of the chamber 138. Reverse movement of the piston 140 causes a dispensation pressure force (not shown) at the port 174 and an aspiration force (not shown) at the port 180. In all other respects, operation of the apparatus 130 is similar to that previously described for the apparatus 10.

The apparatus 130 also includes body sections 182 and 184 that are separable in a manner similar to that previously described for the body sections 80 and 82 of the apparatus 10.

Some advantages of the present invention evident from the foregoing description include a single syringe mechanism that simultaneously aspirates and dispenses equal or different volumes of fluid. The single piston dual chamber arrangement of the apparatus provides a simple, compact design that avoids the need to use two separate syringe mechanisms. The volumes displaced in each of the two chambers of the syringe can be made equal or to a specific ratio by the choice of piston diameter, chamber length and chamber diameter. Separation of the body sections of the syringe permit convenient access to the compression seals, the piston and the syringe chambers. Thus, simple reciprocating movement of the piston provides separate and simultaneous aspiration and dispense functions at separate chambers of the syringe body that operate on separate and isolated fluid samples.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A syringe for simultaneous aspiration and dispensation of fluid comprising,
   a) a syringe body with an interior space including first and second interior chambers of fixed extent that are non-communicable in said syringe body, each of said first and second interior chambers having one and only one port for both inlet and outlet of fluid,
   b) a piston disposed in said syringe body extending through the first and second interior chambers,
   c) said piston having a first section movable in said first interior chamber, a second section movable in said second interior chamber, and a median section joining said first and second piston sections and being movable in said first and second interior chambers, said first and second sections of said piston being of respective diameters that differ from the diameter of the median section of the piston, wherein the median section is of greater or lesser diameter than the diameters of each of the first and second piston sections,
   d) annular compression seal means being provided at a fixed position in the syringe body to embrace the median section of the piston such that said annular compression seal means form a leak-tight seal against the median section of the piston and divides the interior space of said syringe body into said first chamber and said second chamber,
   e) and wherein the first and second piston sections have diameters of less magnitude than the diameter of the median section of the piston,
   f) and wherein the diameter of the first and second sections of the piston are unequal.

2. The syringe as claimed in claim 1 wherein the syringe body includes two body sections with one of said chambers being located in one of said body sections and the other of said chambers being located in the other of said body sections.

3. The syringe as claimed in claim 2 wherein said two body sections are detachably joined together at said annular compression seal means, such that the separation of said two body sections at their detachable junction permits access to the annular compression seal means.

4. The syringe as claimed in claim 1 wherein the annular compression means is at adjacent ends of the first and second chambers, and second and third compression seals are provided at opposite non-adjacent ends of the first and second chambers, to embrace the first and second sections of the piston and form a leak-tight seal against the first and second sections of the piston.

5. The syringe as claimed in claim 1 wherein said annular compression seal means is a single component.

6. The syringe as claimed in claim 5 wherein said annular compression seal means are two components spaced from each other.

7. A syringe for simultaneous aspiration and dispensation of fluid comprising,
   a) a syringe body defining first and second chambers of fixed axial extent that are non-communicable in said syringe body, each said first and second chamber having one and only one port for both inlet and outlet of fluid,
   b) a piston disposed in said syringe body extending through the first and second chambers,
   c) said piston having a first section movable in said first chamber, a second section movable in said second chamber, and a median section joining said first and second piston sections, said median section being movable in said first and second chambers without influencing the size of said first and second chambers, said first and second sections of said piston being of respective diameters that are of greater magnitude than the diameter of the median section of the piston.

8. The syringe as claimed in claim 7 wherein the diameters of the first and second sections of the piston are equal.

9. The syringe as claimed in claim 7 wherein the diameters of the first and second sections of the piston are unequal.

10. A method for simultaneous aspiration and dispensation of fluid comprising,
    a) forming a syringe body with two chambers of fixed axial extent that do not communicate within the syringe body or outside of the syringe body,
    b) providing one and only one port for each chamber to permit each chamber to both aspirate and dispense fluid from the one port in each chamber,
    c) slideably disposing a piston in the syringe body to extend through the first and second chambers,
    d) forming the piston with,
       1) a median section that is movable in both of said first and second chambers,
       2) first and section piston sections that respectively extend from opposite ends of the median section for respective movement in the first and second chambers,
    e) rendering the diameter of the median section different from the diameters of the first and second piston sections, and rendering the diameter of the first and second piston sections unequal, whereby the diameter of the median section is greater or less than the diameters of each of the first and second piston sections,
    f) providing an annular compression seal at a fixed position in the syringe body to embrace the median section of the piston such that the annular compression seal forms a leak-tight seal against the median section of the piston section and thereby separates the first chamber and the second chamber.

11. The method of claim 10, including moving the piston in a first direction to provide an aspiration suction force at one of said chamber ports and to provide a dispensation pressure force at the other said chamber port.

12. The method of claim 11, including moving the piston in a direction opposite the first direction to provide a dispensation pressure force at said one chamber port and to provide an aspiration suction force at the other said chamber port.

13. The method of claim 10, including forming the syringe body in two detachably separate body sections, one detachable body section for each said chamber, and separating the detachable body sections at the compression seal to provide access to the compression seal and to each of said first and second chambers at the area of separation.

* * * * *